US005532350A

United States Patent [19]
Cottrell et al.

[11] Patent Number: 5,532,350
[45] Date of Patent: Jul. 2, 1996

[54] CROSSLINKED POLYSACCHARIDES USEFUL AS ABSORBENT MATERIALS

[75] Inventors: Ian W. Cottrell, Yardley, Pa.; Animesh Goswami, Plainsboro; Manjit S. Chowdhary, New City, both of N.J.

[73] Assignee: Rhone-Poulenc Inc., Cranbury, N.J.

[21] Appl. No.: 196,357

[22] Filed: Feb. 15, 1994

[51] Int. Cl.⁶ .................................. C08B 3/06; C08B 3/22
[52] U.S. Cl. .................................. 536/76; 536/80; 536/82; 536/83; 536/114; 536/115; 536/120; 536/121; 536/123; 604/358; 604/904; 602/56; 106/900
[58] Field of Search ........................ 536/56, 58, 76, 536/80, 82, 83, 114, 115, 120, 121, 123; 604/358, 904; 602/56; 106/900

[56] References Cited

U.S. PATENT DOCUMENTS

| | | | |
|---|---|---|---|
| 3,528,421 | 9/1970 | Valliancourt et al. | 128/284 |
| 3,563,243 | 2/1971 | Lindquist | 128/287 |
| 3,563,978 | 2/1971 | Ochs | 536/121 |
| 3,669,103 | 6/1972 | Harper et al. | 128/156 |
| 3,670,731 | 6/1972 | Harmon | 128/284 |
| 3,686,024 | 8/1972 | Nankee et al. | 117/140 |
| 3,783,872 | 1/1974 | King | 128/290 |
| 3,898,143 | 8/1975 | Assarsson et al. | 204/159 |
| 3,903,889 | 9/1975 | Torr | 128/287 |
| 4,043,952 | 8/1977 | Ganslaw et al. | 536/121 |
| 4,055,184 | 10/1977 | Karami | 128/287 |
| 4,069,177 | 1/1978 | Smith | 524/47 |
| 4,076,663 | 2/1978 | Masuda et al. | 524/47 |
| 4,084,591 | 4/1978 | Takebe et al. | 128/285 |
| 4,333,461 | 6/1982 | Muller | 604/369 |
| 4,605,736 | 8/1986 | Morgan | 536/114 |
| 4,624,868 | 11/1986 | Muller | 427/384 |
| 4,677,201 | 6/1987 | Morgan | 536/114 |
| 4,952,550 | 8/1990 | Wallach et al. | 502/404 |
| 4,959,464 | 9/1990 | Yeh | 536/114 |
| 5,100,933 | 3/1992 | Tanaka et al. | 523/300 |
| 5,242,491 | 9/1993 | Mamada et al. | 106/241 |
| 5,274,018 | 12/1993 | Tanaka et al. | 524/166 |

FOREIGN PATENT DOCUMENTS

| | | |
|---|---|---|
| 0357474 | 3/1990 | European Pat. Off. . |
| 0481225 | 4/1992 | European Pat. Off. . |
| 0556118 | 4/1992 | European Pat. Off. . |

OTHER PUBLICATIONS

Superabsorbent Patents Much More Than Just Diapers, by Bernard J. Obenski, Nonwoven Industry, Nov. 1987 pp. 24–26.
High Gel Strength Cellulosic Absorbent Polymers for Absorbing Meat Fluids in Packaging Applications, Res. Disclosure—1993 May 1993—349—p. 296+.
Chemical Abstract—(A 118C12): 109801K, 1992.
Chemical Abstract—(A 116C2): 11260Z, 1991.

Primary Examiner—Nathan M. Nutter
Attorney, Agent, or Firm—Andrew M. Solomon

[57] ABSTRACT

A solid composition of matter comprising one or more polysaccharides which has been cross-linked with either titanium or zirconium cross-linking agents is provided. The composition demonstrates absorbent properties and is useful in absorbent articles of manufacture. Also provided is a method for preparing the compositions.

25 Claims, No Drawings

CROSSLINKED POLYSACCHARIDES USEFUL AS ABSORBENT MATERIALS

BACKGROUND OF THE INVENTION

1. Field of the Invention

This invention relates to novel absorbent materials, a process for preparing these materials and absorbent articles such as diapers or sanitary napkins containing the absorbent. More specifically, the absorbent materials comprise polysaccharides which have been cross-linked with aluminum, titanium or zirconium cross-linking agents.

2. Technology Description

Many attempts have been described in the patent literature to prepare absorbent materials, i.e. materials which are capable of absorbing many times their weight of water or various body fluids.

The following list is representative of United States patents which have issued in this area: U.S. Pat. No. 3,528,421 (disposable absorbent underpad for hospital patients or similar product, hydrous calcium silicate chemical absorbent); U.S. Pat. No. 3,563,243 (absorbent pads such as diapers, underpads and the like-hydrophilic polymer absorbent); U.S. Pat. No. 3,669,103 (absorbent products containing a hydrocolloidal polymeric absorbent lightly cross-linked polymer such as poly-N-vinyl-pyrrolidone, polyvinyltoluenesulfonate, poly-sulfoethyl acrylate, and others); U.S. Pat. No. 3,686,024 (water absorbent articles coated with a water-swollen gel such as cross-linked partially hydrolyzed polyacrylamide); U.S. Pat. No. 3,670,731 (absorbent dressing using water soluble hydrocolloidal composition); U.S. Pat. No. 3,783,872 (absorbent articles such as diapers, and the like using insoluble hydrogels as the absorbing media); U.S. Pat. No. 3,898,143 (disposable absorbent articles using poly(ethylene oxide) and at least one other water soluble polymer co-crosslinked by high energy irradiation); U.S. Pat. No. 4,055,184 (absorbent pads for disposable diapers, sanitary napkins, bandages or the like using solid, finely-divided mixture of a hydrolyzed starch polyacrylonitrile graft copolymer in acidic form and a non-irritating and non-toxic water-soluble basic material); U.S. Pat. No. 4,069,177 (water absorbing and urine stable stepwise grafted starch-polyacrylonitrile copolymers); U.S. Pat. No. 4,076,663 (water absorbing starch resins); U.S. Pat. No. 4,084,591 (absorber for blood made from filaments of a lower alkyl or a lower hydroxyalkyl substituted cellulose ether).

In U.S. Pat. No. 3,903,889 the patentee describes as an absorbent composition for use in absorbent products a guar gum which is modified with borate anion in an amount sufficient to complex the gel formed from the hydration of guar gum alone. Specifically, the patentee teaches introducing borate ion into the absorbent product in the form of an essentially water insoluble borate-release agent in which the free borate ion is released slowly to the absorbent system and only after the aqueous liquid sought to be absorbed by the product has entered the product itself. It is suggested that the modified guar gum can absorb up to at least 20 times its weight of water to produce a relatively dry non-sticky and inert gel.

U.S. Pat. Nos. 4,333,461 and 4,624,868 are directed to absorbent materials which comprise borate cross-linked polysaccharides. The enabled polysaccharides are guar gum and its derivatives.

U.S. Pat. No. 4,952,550 is directed to particulate absorbent materials which are carboxylated cellulosic materials. More specifically, the materials are cellulosic base materials which are reacted with a cross-linking agent and a hydrophobicity agent. Preferred cross-linking agents include metals such as aluminum, iron or chromium. Similarly, Research Disclosure 349,296 suggests the use of aluminum cross-linked cellulose gums as absorbent materials.

Other known absorbent materials include those derived from acrylic polymers and those derived from amino acids.

Except for the polyacrylates and starch grafted acrylates, with respect to their application for absorbing or holding fluids such as in diapers, sanitary napkins, bandages, gloves, sporting goods, pet litter and the like the absorbent materials and absorbent products described in these patents have not been commercially acceptable. Such problems as insufficient absorbing capacity, insufficient rigidity of the swollen gel, breakdown of the gel structure upon contact with saline fluids, incompatibility with absorbent articles, still exist.

U.S. Pat. Nos. 4,605,736 and 4,677,201 are directed to cross-linking polygalactomannans with a titanium based cross-linking agent. The in situ cross-linking reaction is performed in an aqueous environment and the polygalactomannan is not recovered. These aqueous systems are suggested for use in oil recovery.

U.S. Pat. No. 4,959,464 is directed to the production of aluminum cross-linked derivatized polygalactomannans. The resulting products are suggested for use as thickening agents which readily hydrate under alkaline pH conditions.

Despite the above teachings, there still exists a need in the art for novel compositions which have functionality as absorbent materials.

BRIEF SUMMARY OF THE INVENTION

In accordance with the present invention novel solid compositions are provided which have functionality as absorbent materials. More specifically, the solid compositions comprise polysaccharides which have been cross-linked with either titanium or zirconium cross-linking agents.

One embodiment of the present invention provides a solid composition of matter comprising one or more polysaccharides which have been cross-linked with either titanium or zirconium cross-linking agents.

Particularly preferred polysaccharides include cellulose materials, and polygalactomannans such as guar gum and locust bean gum. Particularly preferred are the use of derivatized guar polymers.

Another embodiment of the present invention provides absorbent solid compositions comprising one or more polysaccharides which have been cross-linked with either aluminum, titanium or zirconium cross-linking agents with the proviso that if said one or more polysaccharides comprises cellulose gum or carboxymethyl cellulose, said cross-linking agent is not an aluminum cross-linking agent.

An additional embodiment of the present invention comprises an absorbent article of manufacture where the article includes one or more polysaccharides which have been cross-linked with either aluminum, titanium or zirconium cross-linking agents with the proviso that if said one or more polysaccharides comprises cellulose gum or carboxymethyl cellulose, said cross-linking agent is not an aluminum cross-linking agent.

Particularly preferred article of manufactures include diapers, feminine hygiene articles, wound dressings, pet litter and the like.

Still another embodiment of the present invention provides a process for preparing the novel compositions of the present invention. This embodiment comprises adding a titanium or zirconium cross-linking agent to a solution including one or more polysaccharides, allowing said polysaccharide to cross-link, and drying said cross-linked polysaccharide to yield a solid composition.

Accordingly, it is an object of the present invention to provide a novel composition which has absorbent properties.

Another object of the present invention is to provide novel absorbent compositions.

Still another object of present invention is to provide novel absorbent articles of manufacture.

Yet another object of present invention is to provide a novel process for preparing the inventive compositions.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

The present invention provides solid absorbent compositions comprising polysaccharides which have been cross-linked with either aluminum, zirconium or titanium cross-linking agents.

The compositions are cross-linked polysaccharides, preferably polygalactomannans. The polygalactomannans have a degree of substitution and/or a molar substitution of between about 0 and about 3.0.

The polygalactomannans are naturally occurring polysaccharides composed principally of galactose and mannose units and are usually found in the endosperm of leguminous seeds, such as guar, locust bean, honey locust, flame tree, and the like. Guar flour, for example, is composed mostly of a galactomannan which is essentially a straight chain mannan with single membered galactose branches. The mannose units are linked in a 1-4-β-glycosidic linkage and the galactose branching takes place by means of a 1-6 linkage on mannose units in an irregular manner. The ratio of galactose to mannose in the guar polymer is about one to two.

Locust bean gum is also a polygalactomannan gum of similar molecular structure in which the ratio of galactose to mannose is one to four. Guar and locust bean gum are the preferred sources of the polygalactomannans, principally because of the commercial availability thereof.

In use the polygalactomannan may be either in its natural state (i.e., pure guar gum or locust bean gum) or may be derivatized. Derivatized polygalactomannans include one or more non-ionic and/or ionic groups. Examples of such polygalactomannans include hydroxypropyl guar, hydroxyethyl guar, carboxymethyl guar, carboxymethyl hydroxypropyl guar and the like having varying degrees of substitution and molar substitution. Such derivatized polygalactomannans are sold by Rhône-Poulenc Inc. under the trade names Jaguar 8000 (hydroxypropyl guar), Jaguar 8710 (carboxymethyl guar) and Jaguar 8600 (carboxymethylhydroxypropyl guar). Many commercially available starting guar materials may contain small amounts of additives such as borax, glyoxal and the like. These starting materials are expressly covered as constituting part of the present invention.

The term "degree of substitution" as employed herein is the average substitution of functional groups per anhydro sugar unit in the polygalactomannan gums. In guar gum, the basic unit of the polymer consists of two mannose units with a glycosidic linkage and a galactose unit attached to a hydroxyl group of one of the mannose units. On the average, each of the anhydro sugar units contains three available hydroxyl sites. A degree of substitution of three would mean that all of the available hydroxyl sites have been esterified with functional groups. A particularly preferred functional group is the carboxymethyl group, with good results obtained with starting materials having a degree of substitution of between about 0.0 and about 3.0, specifically including materials having a degree of substitution ranging from about 0.10 to about 0.15.

Similarly, the term "molar substitution" as employed herein is the average number of moles of functional groups per anhydro sugar unit in the polygalactomannan gum. A particularly preferred functional group is the hydroxypropyl group, with good results obtained with starting materials having a molar substitution of between about 0.0 and about 3.0. In a preferred embodiment the resulting polysaccharide is carboxymethyl hydroxypropyl guar having a molar substitution of hydroxypropyl groups of between about 0.25 and about 0.35 and a degree of substitution of carboxymethyl groups of between about 0.10 and about 0.15.

Alternative polysaccharide materials which may be selected as the starting material include starches, celluloses and xanthan gum. Examples of starches include both natural and modified starches, such as dextrinated, hydrolyzed, oxidized, cross-linked, alkylated, hydroxyalkylated, acetylated, or fractionated (e.g., amylose and amylopectin). The starch may be of any origin, for example, corn starch, wheat starch, potato starch, tapioca starch, sago starch, rice starch, waxy corn starch or high-amylose corn starch.

Examples of celluloses include hydroxyethyl cellulose, hydroxypropyl cellulose, cellulose gum, carboxymethyl cellulose and alkyl celluloses. Similar to the polygalactomannans, these derivatized materials may have a degree of substitution ranging from about 0.0 to about 3.0.

The cross-linking agent selected is either an aluminum, titanium or zirconium cross-linking material, including mixtures thereof. The agents may be inorganic or organometallic compounds of aluminum, titanium or zirconium. Particularly preferred are salts of aluminum, titanium or zirconium. The aluminum, titanium or zirconium metals may form the cationic and/or anionic portion of the compound. Examples of suitable salts include the acetates, alkoxides such as isopropoxides, hydroxides, halides, lactates, carbonates, nitrates, sulfates and the like. Also useful within the scope of the present invention are the alkali metal and ammonium salts of the respective aluminum, titanium or zirconium cross-linking materials, such as the sodium, potassium or ammonium salts.

Examples of specifically useful cross-linking agents include aluminum acetate, aluminum sulfate, aluminum isopropoxide, aluminum hydroxide, sodium zirconium lactate, zirconium lactate, zirconium acetate, potassium zirconium carbonate, ammoniacal zirconium carbonate, aluminum chloride, titanium acetate and mixtures thereof.

It is even possible to use other cross-linking agents in combination with the aluminum, titanium or zirconium cross-linking agents as long as one of these materials is present. Examples of such auxiliary cross-linking agents include borate materials such as borax, the key criteria being that at least one of the aluminum, titanium or zirconium cross-linking agents be included. While not wishing to be bound to any specific theory, the inventors hypothesize that the zirconium, aluminum or titanium cross-linking agents provide added strength to a cross-linking formulation that the auxiliary cross-linking agent does not possess.

To produce the compositions of the present invention, a solution or dispersion of the polysaccharide is prepared by adding the polysaccharide to a solvent. In practice water is the preferred solvent in the polysaccharide solution although other solvents such as alcohols, ethers, glycols, hydrocarbons and mixtures thereof may be used. Addition of the polysaccharide typically takes place at temperatures ranging from about 20° C. to about 90° C., with temperatures between about 40° C. to about 50° C. being most preferred.

The amount of polysaccharide added to the solvent is not critical, the primary consideration being that the polysaccharide be fully wetted (hydrated when the solvent is water). The amount of solvent generally will range from about 1 part to about 200 parts water per part of polysaccharide, preferably from about 30 parts to about 120 parts water per part of polysaccharide. The polysaccharide-solvent solution is allowed to mix for a time sufficient until the polysaccharide is at least substantially completely wetted, preferably completely wetted. To enhance the wetting procedure the mixture may be stirred. Generally from about 5 minutes to about 2 hours will be sufficient for the polysaccharide to be completely wetted.

Thereafter, the aluminum, titanium or zirconium cross-linking agent, including optional auxiliary cross-linking agent is added to the solution in amounts ranging from about 0.01 parts to about 50 parts, more preferably about 0.10 to about 10 parts per 100 parts of polysaccharide. The agent may be added to the solution in neat form, or, more preferably, in a carder liquid which is preferably the same as the solvent of the solution. This will typically be water. Cross-linking occurs by thoroughly stirring the solution and is demonstrated by the formation of a thixotropic mass. The time required for cross-linking the polysaccharide typically takes between about 5 seconds and about 2 hours, with times ranging from about 1 minute and about 30 minutes being especially preferred.

Other methods can be used to cross-link the solution such as by adjusting pH, heating and other methods known by those skilled in the art. The rate of cross-linking depends upon such factors as the temperature, pH, amount, rate and degree of mixing, concentration of the cross-linking agent and the like. The cross-linking reaction is completed when the viscosity of the resulting thickened gel-like mass no longer changes or becomes very high. Accordingly, the cross-linked polysaccharide gum may have a consistency ranging from a coherent slowly pourable gel through first stage gelling or gelation in which the thickened mass is no longer pourable but does not have dimensional stability and will spread if unconfined or second stage gelling in which the gel will have some dimensional stability and will temporarily hold a shape but will spread if unconfined for a short period of time.

To yield the solid compositions, the gel is allowed to dry (i.e., removal of moisture) by means known in the art so that the final moisture content of the composition is less than 20 percent, more preferably less than 15 percent and most preferably less than 10 percent by weight. They include air drying, drum drying, filtering, evaporative drying, centrifuging, flash grinding, addition of solvents, freeze drying and the like.

Once dried, the solid compositions may be grounded to yield particulates having a particle size as desired. The size of the particulates, preferably granular particles are primarily dictated by the desired final use. Similarly, the shape of the final compositions may be as desired. Alternatively, the product may be dried as a thin film, laminate, or sheet. Shapes including spherical particles, flakes and the like are clearly contemplated as falling within the scope of the invention. The key selection criteria for the final shape of the particulates is primarily dictated by the intended final use for the absorbent material.

When liquids are added to these synthesized compositions, the compositions demonstrate an excellent balance of absorbency and gel strength. As such, they are considered good candidates for absorbent materials having a wide variety of use. Examples of such uses include diapers, adult incontinence articles, feminine hygiene articles, wound dressings, pet litter, agricultural uses such as hydromulching and soil amendment, automotive filters, underground cables, waste disposal, sporting goods, gloves such as work gloves, cosmetic gloves and batteries.

In the preferred mode, the above absorbent articles are designed for throw-away single use applications and they are used in contact with body fluids such as urine, catamenial discharge, perspiration and the like. In its broadest sense, therefore, the present invention provides absorbent articles in which absorbent particles of the cross-linked polysaccharide are contained in, on, or carded by a substrate material, the articles being capable of being held in contact with the body of the user such that the absorbent particles are in contact with body fluids exuded by the body either directly or after passing through a body-contacting cover sheet.

In comparison to the known polyacrylate based materials, the inventive compositions offer advantages because they are more environmentally friendly as they are derived from naturally occurring materials, are biodegradable and less sensitive to salts. Further, as compared to polygalactomannans which have been cross-linked by borate materials as suggested in U.S. Pat. Nos. 4,333,461 and 4,624,868, and as shown in the Examples to follow, the inventive compositions demonstrate superior performance in terms of absorbency and gel strength.

The invention is described in greater detail by the following non-limiting examples.

COMPARATIVE EXAMPLE 1

To 2 liters of water at 45°–50° C., carboxymethyl hydroxypropyl guar (20 g) is added with rapid stirring. The stirring is continued for 1 hour. A solution of borax (2 g) in water (20 ml) is added. The mixture is stirred for 15 minutes and poured in a stainless steel tray. The contents of the tray are allowed to air dry and are pulverized in a grinder. The saline (0.9% sodium chloride solution) absorbency properties are shown in Table 1. The sheep blood (citrated) absorbency properties are shown in Table 2.

COMPARATIVE EXAMPLE 2

To 2 liters of water at 45°–50° C., carboxymethyl hydroxypropyl guar (20 g) is added with rapid stirring. The stirring is continued for 1 hour. A solution of borax (5 g) in water (50 ml) is added. The mixture is stirred for 15 minutes and poured in a stainless steel tray. The contents of the tray are allowed to air dry and are pulverized in a grinder. The saline (0.9% sodium chloride solution) absorbency properties are shown in Table 1. The sheep blood (citrated) absorbency properties are shown in Table 2.

EXAMPLE 1

To 2 liters of water at 45°–50° C., carboxymethyl guar (20 g) is added with rapid stirring. The stirring is continued for 1 hour. A solution (2.25 ml) of sodium zirconium lactate (zirconium content 5.4%) in water (10 ml) is added. The mixture is stirred for 15 minutes and poured in a stainless steel tray. The contents of the tray are allowed to air dry and pulverized in a grinder. The saline absorbency properties are in Table 1. The sheep blood absorbency properties are in Table 2.

EXAMPLE 2

To 2 liters of water at 45°–50° C., carboxymethyl hydroxypropyl guar (20 g) is added with rapid stirring. The stirring is continued for 1 hour. A solution (2.5 ml) of sodium zirconium lactate (zirconium content 5.4%) in water (10 ml) is added. The mixture is stirred for 15 minutes and poured in a stainless steel tray. The contents of the tray are allowed to air dry and pulverized in a grinder. The saline absorbency properties are in Table 1.

EXAMPLE 3

To 2 liters of water at 45°–50° C., carboxymethyl hydroxypropyl guar (20 g) is added with rapid stirring. The stirring is continued for 1 hour. A solution (2.0 ml) of sodium zirconium lactate (zirconium content 5.4%) in water (10 ml) is added. The mixture is stirred for 15 minutes and poured in a stainless steel tray. The contents of the tray are allowed to air dry and pulverized in a grinder. The sheep blood absorbency properties are in Table 2.

EXAMPLE 4

To 2 liters of water at 45°–50° C., carboxymethyl guar (20 g) is added with rapid stirring. The stirring is continued for 1 hour. A solution (4 ml) of ammoniacal complex of zirconium lactate and acetate (zirconium content 8.9%) in water (10 ml) is added. The mixture is stirred for 15 minutes and poured in a stainless steel tray. The contents of the tray are allowed to air dry and pulverized in a grinder. The saline absorbency properties are in Table 1.

EXAMPLE 5

To 2 liters of water at 45°–50° C., carboxymethyl guar (20 g) is added with rapid stirring. The stirring is continued for 1 hour. A solution of 2 g of potassium zirconium carbonate (zirconium content 28.1% ) in water (20 ml) is added. The mixture is stirred for 15 minutes and poured in a stainless steel tray. The contents of the tray are allowed to air dry and pulverized in a grinder. The saline absorbency properties are in Table 1.

EXAMPLE 6

To 2 liters of water at 45°–50° C., carboxymethyl guar (20 g) is added with rapid stirring. The stirring is continued for 1 hour. A solution of 2.19 g of ammoniaca/zirconium carbonate containing tartaric acid (zirconium content 14.8%) in water (20 ml) is added. The mixture is stirred for 15 minutes and poured in a stainless steel tray. The contents of the tray are allowed to air dry and pulverized in a grinder. The saline absorbency properties are in Table 1.

EXAMPLE 7

To 2 liters of water at 45°–50° C., carboxymethyl guar (20 g) is added with rapid stirring. The stirring is continued for 1 hour. A solution (2.5 ml) of sodium zirconium lactate (zirconium content 5.4%) in water (10 ml) is added. The mixture is stirred for 15 minutes. The thick mixture is drum dried (between two rolling drums at elevated temperature). The dried material is pulverized in a grinder. The saline absorbency properties are in Table 1.

EXAMPLE 8

To 2 liters of water at 45°–50° C., carboxymethyl guar (20 g) is added with rapid stirring. The stirring is continued for 1 hour. A solution of 1.43 g of aluminum chloride in water (20 ml) is added. The mixture is stirred for 15 minutes and poured in a stainless steel tray. The contents of the tray are allowed to dry in air. The dried material is pulverized in a grinder. The saline absorbency properties are in Table 1.

EXAMPLE 9

To 2 liters of water at 45°–50° C., carboxymethyl guar (20 g) is added with rapid stirring. The stirring is continued for 1 hour. A solution (2 ml) of Tyzor 131 titanate (from DuPont, containing 3.54% Titanium) in water (8 ml) is added. The mixture is stirred for 15 minutes and poured in a stainless steel tray. The contents of the tray are allowed to dry in air. The dried material is pulverized in a grinder. The saline absorbency properties are in Table 1.

EXAMPLE 10

To 2 liters of water at 45°–50° C., carboxymethyl hydroxypropyl guar (20 g) is added with rapid stirring. The stirring is continued for 1 hour. A solution (5.0 ml) of sodium zirconium lactate (zirconium content 5.4%) in water (10 ml) and a solution of borax (5 g) in water (50 ml) is added. The mixture is stirred for 15 minutes and poured in a stainless steel tray. The contents of the tray are allowed to air dry and pulverized in a grinder. The saline absorbency properties are in Table 1 and the sheep blood absorbency properties are in Table 2.

EXAMPLE 11

To 2 liters of water at 45°–50° C., carboxymethyl hydroxypropyl guar (20 g) is added with rapid stirring. The stirring is continued for 1 hour. A solution of sodium zirconium lactate (2.0 ml zirconium content 5.4%) and Tyzor 131 titanate (0.5 ml, containing 3.54% titanium) in water (10 ml) is added. The mixture is stirred for 15 minutes and poured in a stainless steel tray. The contents of the tray are allowed to air dry and pulverized in a grinder. The saline absorbency properties are in Table 1.

EXAMPLE 12

To 2 liters of water at 45°–50° C., carboxymethyl hydroxypropyl guar (20 g) is added with rapid stirring. A solution (5.0 ml) of sodium zirconium lactate (zirconium content 5.4%) in water (10 ml) is added. The mixture is stirred for 15 minutes and poured in a stainless steel tray. The contents of the tray are allowed to air dry and pulverized in a grinder. The saline absorbency properties are in Table 1.

EXAMPLE 13

To 2 liters of water at 45°–50° C., carboxymethyl hydroxypropyl guar (20 g) is added with rapid stirring. The stirring is continued for 1 hour. A solution (2.5 ml) of sodium zirconium lactate (zirconium content 5.4%) in water (10 ml) is added. The mixture is stirred for 15 minutes. The mixture is freeze dried. The freeze dried material is pulverized. The saline absorbency properties of the material are in Table 1.

EXAMPLE 14

To 2 liters of water at 45°–50° C., carboxymethyl hydroxypropyl guar (20 g) is added with rapid stirring. The stirring is continued for 1 hour. The pH of the solution is adjusted to 5.0 by the addition of acetic acid. A solution (5.0 ml) of sodium zirconium lactate (zirconium content 5.4%) in water (10 ml) is added. The mixture is stirred for 15 minutes and poured in a stainless steel tray. The contents of the tray are allowed to air dry and pulverized in a grinder. The reaction is repeated at pHs 8.5, 8.75, 9.0 and 9.5.

EXPERIMENTAL TESTING

Test Procedure

Particles of size 35–50 mesh are used for testing. Saline solution is 0.9% solution of sodium chloride in distilled water. Sheep blood is citrated.

Absorbency: To test for absorbency, a nylon bag is prepared using 100 mesh nylon cloth. The test material (approximately 200 mg) is weighed and poured in the bag. The open side of the bag is closed. The bag containing the material is immersed in saline solution (or sheep blood for blood absorbency). After one hour, the bag is taken out from the solution (or sheep blood). The bag is hanged for 30 minutes and weighed to determine the amount of saline solution (or sheep blood) absorbed by the material. The amount of saline solution (or sheep blood) in grams absorbed by one gram of material is defined as the absorbency.

Centrifuge Retention Capacity: To test for centrifuge retention capacity, the nylon bag containing the saline (or sheep blood) absorbed material from the above experiment is placed over some paper towels inside the basket of a centrifuge (Beckman TJ-6). The centrifuge is operated at 1600 rpm for 3 minutes. The absorbed material in the bag is weighed after centrifuging to determine the amount of saline solution (or sheep blood) retained. The amount of saline solution (or sheep blood) in grams retained by one gram of material is the Centrifuge Retention Capacity (CRC).

Absorbency Under Load: To test absorbency under load, one side of a small cylinder is closed by a stainless steel screen of 100 mesh. Four small pins are attached to the cylinder in such a way that the cylinder could stand on the pins allowing liquid to come through the nylon screen. A small amount (100 mg) of material is evenly distributed on the nylon screen inside the cylinder. The top of the material is covered with a plexiglass disk and a weight of 100 g is placed on the disk to provide a load of 20 g/cm$^2$ on the material. The cylinder is placed in a container containing the saline solution. After one hour, the cylinder is removed and weighed to determine the amount of saline solution absorbed under the load. The amount of saline solution in grams absorbed under the load by one gram of material is defined as the Absorbency Under Load (AUL).

Gel Strength: To test gel strength, the saline solution absorbed material is prepared in the same way as mentioned under absorbency before. The absorbed material is placed between the parallel plates of a Rheometrics Dynamic Spectrometer II. The dynamic shear modulus G° at 1 Hz is reported as the Gel Strength.

Results of the above testing are shown in Tables 1 and 2.

TABLE 1

Absorbency Properties in Saline solution

| Materials obtained from Example | Absorbency (g/g) | CRC (g/g) | AUL (g/g) | Gel Strength (Dynes/cm$^2$) |
|---|---|---|---|---|
| Comparative Example 1 | 61* | ** | 16 | 171 |
| Comparative Example 2 | 68* | ** | 15.5 | 303 |
| Example 1 | 48.5 | 34 | 19 | 17770 |
| Example 2 | 42 | 26 | 19 | 16040 |
| Example 4 | 41 | 30.5 | 13 | – |
| Example 5 | 48 | 35 | 15.5 | – |
| Example 6 | 25.5 | 16.5 | 18.5 | – |
| Example 7 | 45 | 25 | 18.4 | – |
| Example 8 | 32.2 | 19 | 15.4 | 17680 |
| Example 9 | 35 | 23 | 18 | 10780 |
| Example 10 | 58 | 47 | 14 | 2120 |
| Example 11 | 38 | 25 | 21 | 10590 |
| Example 12 | 28 | 14 | 17.5 | 28820 |
| Example 13 | 44 | 23.5 | 18.5 | 16040 |

CRC = Centrifuge Retention Capacity
AUL = Absorbency Under Load

TABLE 2

Sheep Blood Absorbency Properties

| Materials obtained from Example | Absorbency (g/g) | Centrifuge Retention Capacity (g/g) |
|---|---|---|
| Comparative Example 1 | 22.5 | 14 |
| Comparative Example 2 | 47* | ** |
| Example 1 | 28 | 18 |
| Example 3 | 35 | 24 |
| Example 10 | 43 | 27 |

*A significant amount of slimy material is on the outside of the bag and dripping. This is only observed for these examples.
**CRC could not be determined since all material came out of the bag under centrifugal force
– not measured The above data demonstrate that the inventive compositions have an excellent balance of absorbency and gel strength. As compared to the borax only cross-linked composition (Comparative Examples 1 and 2), the inventive compositions provided superior performance in terms of centrifuge retention capacity, absorbency under load and gel strength. They should be excellent candidates for commercial absorbent materials.

It should further be noted that mixtures of cross-linking agents also produce excellent results as long as at least one of the cross-linking agents is a zirconium, titanium or aluminum cross-linking agent. Examples 10 and 11 demonstrate this.

Having described the invention in detail and by reference to the preferred embodiments thereof, it will be apparent that modifications and variations are possible without departing from the scope of the appended claims.

What is claimed is:

1. A solid composition of matter comprising one or more water-insoluble polygalactomannans which has been crosslinked with either titanium or zirconium cross-linking agents or mixtures thereof.

2. The composition according to claim 1 wherein said polygalactomannan comprises guar gum.

3. The composition according to claim 2 wherein said guar gum is derivatized.

4. The composition according to claim 3 wherein said guar gum is carboxymethyl guar gum or carboxymethyl hydroxypropyl guar gum.

5. The composition according to claim 2 wherein said cross-linking agent comprises a zirconium cross-linking agent.

6. The composition according to claim 1 which is in the physical form of particles.

7. The composition according to claim 1 which is in the physical form of flakes, films, sheets or laminates.

8. Absorbent solid compositions comprising one or more water-insoluble polygalactomannans which have been cross-linked with either aluminum, titanium or zirconium cross-linking agents or mixtures thereof.

9. The composition according to claim 8 wherein said polygalactomannan comprises guar gum.

10. The composition according to claim 9 wherein said guar gum is derivatized.

11. The composition according to claim 10 wherein said guar gum is carboxymethyl guar gum or carboxymethyl hydroxypropyl guar gum.

12. The composition according to claim 9 wherein said cross-linking agent comprises a zirconium cross-linking agent.

13. The composition according to claim 8 which is in the physical form of particles.

14. The composition according to claim 8 which is in the physical form of flakes, films, laminates or sheets.

15. An absorbent article of manufacture where the article includes a solid absorbent composition comprising one or more water-insoluble polygalactomannans which have been cross-linked with either aluminum, titanium or zirconium cross-linking agents or mixtures thereof.

16. The article according to claim 15 wherein said article is selected from the group consisting of diapers, adult incontinence articles, feminine hygiene articles, wound dressings, pet litter, hydromulching aids, soil amendment aids, automotive filters, underground cables, waste disposal aids, sporting goods, work gloves, cosmetic gloves and batteries.

17. The article according to claim 16 wherein said polygalactomannan comprises guar gum.

18. The article according to claim 17 wherein said guar gum is derivatized.

19. The article according to claim 18 wherein said guar gum is carboxymethyl guar gum or carboxymethyl hydroxypropyl guar gum.

20. The article according to claim 17 wherein said cross-linking agent comprises a zirconium cross-linking agent.

21. The article according to claim 16 wherein said polygalactomannan is in the physical form of particles.

22. The article according to claim 16 wherein said polygalactomannan is in the physical form of flakes, films, laminates or sheets.

23. Absorbent solid compositions comprising one or more water-insoluble polygalactomannans which have been cross-linked in solution form with either aluminum, titanium or zirconium cross-linking agents or mixtures thereof.

24. An absorbent article of manufacture where the article includes a solid absorbent composition comprising one or more water-insoluble polygalactomannans which have been cross-linked in solution form with either aluminum, titanium or zirconium cross-linking agents or mixtures thereof.

25. The article according to claim 24 wherein said article is selected from the group consisting of diapers, adult incontinence articles, feminine hygiene articles, wound dressings, pet litter, hydromulching aids, soil amendment aids, automotive filters, underground cables, waste disposal aids, sporting goods, work gloves, cosmetic gloves and batteries.

* * * * *